US008835369B2

(12) United States Patent
Cifelli

(10) Patent No.: US 8,835,369 B2
(45) Date of Patent: Sep. 16, 2014

(54) ODORLESS ACETONE-FREE NAIL POLISH REMOVING COMPOSITION

(75) Inventor: Dana Cifelli, Clark, NJ (US)

(73) Assignee: L'Oreal, Paris (FR)

( * ) Notice: Subject to any disclaimer, the term of this patent is extended or adjusted under 35 U.S.C. 154(b) by 134 days.

(21) Appl. No.: 13/487,639

(22) Filed: Jun. 4, 2012

(65) Prior Publication Data

US 2013/0319462 A1 Dec. 5, 2013

(51) Int. Cl.
C11D 3/43 (2006.01)
C11D 3/20 (2006.01)

(52) U.S. Cl.
CPC ............... *C11D 3/43* (2013.01); *C11D 3/2093* (2013.01)
USPC .......................................... 510/118; 510/407

(58) Field of Classification Search
CPC .............................. C11D 3/433; C11D 3/2093
USPC .................................. 510/118, 407
See application file for complete search history.

(56) References Cited

U.S. PATENT DOCUMENTS

| | | | |
|---|---|---|---|
| 3,384,592 A | 5/1968 | Weems | |
| 5,258,070 A | 11/1993 | Monteleone et al. | |
| 5,346,692 A | 9/1994 | Wohlrab et al. | |
| 5,827,807 A | 10/1998 | Aoshima et al. | |
| 6,585,963 B1 | 7/2003 | Quan et al. | |
| 6,936,264 B2 * | 8/2005 | Glenn et al. | 424/401 |
| 6,998,371 B2 | 2/2006 | Tavares | |
| 7,074,746 B2 | 7/2006 | Fujii | |
| 8,138,106 B2 * | 3/2012 | Hamed et al. | 442/123 |
| 8,262,634 B1 * | 9/2012 | Gray et al. | 604/385.05 |
| 2002/0159960 A1 * | 10/2002 | Scancarella et al. | 424/64 |
| 2004/0022822 A1 * | 2/2004 | Poret | 424/401 |
| 2004/0033254 A1 * | 2/2004 | Song et al. | 424/449 |
| 2004/0198630 A1 * | 10/2004 | Schmid et al. | 510/499 |
| 2007/0287647 A1 | 12/2007 | Hadry et al. | |
| 2008/0207933 A1 * | 8/2008 | Bigorra Llosas et al. | 554/52 |
| 2008/0241089 A1 * | 10/2008 | Banowski et al. | 424/65 |
| 2009/0068255 A1 * | 3/2009 | Yu et al. | 424/450 |
| 2009/0162446 A1 * | 6/2009 | Gatto et al. | 424/489 |
| 2009/0191138 A1 | 7/2009 | Dechow | |
| 2010/0204076 A1 | 8/2010 | Cheng | |

FOREIGN PATENT DOCUMENTS

| | | |
|---|---|---|
| CN | 101112351 A | 1/2008 |
| CN | 101953769 A | 1/2011 |
| DE | 202009000908 U1 | 6/2009 |
| JP | 2006182674 A | 7/2006 |

OTHER PUBLICATIONS

English Abstract of CN-101953769-A.
English Abstract of CN-101112351-A.
English Abstract of JP-2006182674-A.
Notification of Transmittal of the International Search Report and the Written Opinion of the International Searching Authority, or the Declaration, International Application No. PCT/US2013/042406, mailed Nov. 12, 2013, including International Search Report and Written Opinion of the ISA.

* cited by examiner

*Primary Examiner* — Gregory Webb
(74) *Attorney, Agent, or Firm* — Novak Druce Connolly Bove + Quigg LLP

(57) ABSTRACT

One aspect of the present invention comprises a nail polish removing composition that is essentially free of acetone and ethyl acetate, and is essentially free of odor. The composition includes at least one triester of glycerol and $C_2$-$C_5$ carboxylic acid, at least one $C_3$-$C_5$ glycol, at least one $C_4$-$C_6$ cyclic carbonate, and, optionally, at least one colorant. Another aspect of the present invention is a method of removing nail polish, comprising providing the nail polish removing composition; immersing an absorbent material in the composition, wherein the absorbent material absorbs the composition; contacting the absorbent material to nail polish for a time sufficient to plasticize the nail polish film; and removing the plasticized nail polish film by mechanically rubbing with the absorbent material, wherein the composition comprises one or more phases.

19 Claims, No Drawings

ODORLESS ACETONE-FREE NAIL POLISH REMOVING COMPOSITION

BACKGROUND OF THE INVENTION

Organic solvents, such as acetone and ethyl acetate, are typically used to remove nail polish. While such organic solvents are generally effective in removing most types of nail polish, consumers do not consider them desirable because, inter alia, the organic solvents have a strong odor and are harsh on the nail and skin near the nail.

Acetone, for example, is an organic solvent capable of dissolving nail polish effectively, and is a well-known component of nail polish removers. However, acetone can also remove moisture, and thus the nail and the skin near the nail may appear white and dry after contact with acetone-based removers. Furthermore, acetone has a distinct odor that some users find objectionable; and nail polish removers having acetone at 60% to 70% are flammable.

Another example of an organic solvent that can also be, and commonly is, used in nail polish removers is ethyl acetate. While ethyl acetate is not as strong of a solvent as acetone, it remains effective in removing nail polish, and thus is commonly regarded as an alternative to acetone. Ethyl acetate is also slightly less harsh to the nail and skin near the nail in comparison with acetone. Furthermore, ethyl acetate is less volatile than acetone, but its odor is still significant and generally objectionable.

Further non-acetone nail polish removers may contain solvents such as methyl acetate, methyl alcohol, ethyl alcohol, methyl diglycol, and butyl diglycol. These solvents have reduced odors but may cause skin irritation on prolonged use. Also, some solvents, such as methyl alcohol, are considered hazardous to health.

Nail polish remover compositions that do not utilize acetone have been attempted. For example, a nail polish remover according to U.S. Pat. No. 6,998,371 describes the use of esters of fatty acids having 16 to 18 carbon atoms, lower alkyl lactate and a naturally occurring wax. However, while the composition according to the '371 patent is acetone free, it generally leaves an oily feel on the nail and leaves the nail looking unsightly. Another example is a nail polish remover according to U.S. Patent Application Publication No. 2007/0287647 that describes the use of isobutyl nitrite and butylated linseed oil as active ingredients for nail polish removal. However, while the '647 Publication does not use acetone or ethyl acetate, the main ingredient is isobutyl nitrite, which is a known inhalant recreational drug.

Therefore, there remains a need for a nail polish removing composition that is essentially odorless and is essentially free of acetone and ethyl acetate.

BRIEF SUMMARY OF THE INVENTION

One aspect of the present invention is a nail polish removing composition that includes at least one triester of glycerol and a $C_2$-$C_5$ carboxylic acid, at least one $C_3$-$C_5$ glycol, at least one $C_4$-$C_6$ cyclic carbonate, and optionally at least one colorant, wherein the composition is essentially free of acetone and ethyl acetate, and wherein the composition is essentially free of odor.

According to one embodiment, the at least one triester of glycerol and $C_2$-$C_5$ carboxylic acid is selected from the group consisting of triacetin, glycerol tripropionate, glycerol tributyrate and glycerol trivalerate. According to a further embodiment, the at least one triester of glycerol and $C_2$-$C_5$ carboxylic acid is triacetin. The composition of the present invention may comprise at least one triester of glycerol and $C_2$-$C_5$ carboxylic acid in a range from about 5% to about 50% by weight, based on the total weight of the composition.

According to one embodiment, the at least one $C_3$-$C_5$ glycol is selected from the group consisting of 1,2-propylene glycol, 1,2-butylene glycol and 1,2-pentylene glycol. According to a further embodiment, the at least one $C_3$-$C_5$ glycol is propylene glycol. The composition of the present invention may comprise the at least one $C_3$-$C_5$ glycol in a range from about 10% to about 30% by weight, based on the total weight of the composition.

According to one embodiment, the at least one $C_4$-$C_6$ cyclic carbonate is selected from the group consisting of propylene carbonate, butylene carbonate and pentylene carbonate. In a further embodiment, the at least one $C_4$-$C_6$ cyclic carbonate is propylene carbonate. The composition of the present invention may comprise the at least one $C_4$-$C_6$ cyclic carbonate in a range from about 50% to about 75% by weight, based on the total weight of the composition.

In one embodiment, the at least one triester of glycerol and $C_2$-$C_5$ carboxylic acid ranges from about 5% to about 50% by weight, the at least one $C_3$-$C_5$ glycol ranges from about 10% to about 30% by weight, the at least one $C_4$-$C_6$ cyclic carbonate ranges from about 50% to about 75% by weight, and the at least one colorant optionally ranges from 0.01% to about 2% by weight, wherein the weight percentages are based on the total weight of the composition.

In another embodiment, the at least one triester of glycerol and $C_2$-$C_5$ carboxylic acid comprises triacetin, the at least one $C_3$-$C_5$ glycol comprises propylene glycol, and the at least one $C_4$-$C_6$ cyclic carbonate comprises propylene carbonate.

According to one embodiment of the present invention, triacetin ranges from 5% to about 50% by weight, propylene glycol ranges from about 10% to about 30% by weight, and propylene carbonate ranges from about 50% to about 75% by weight, wherein the weight percentages are based on the total weight of the composition.

In an embodiment of the present invention, the composition further comprises at least one ester of a $C_2$-$C_5$ alcohol and myristic acid. The at least one ester of the $C_2$-$C_5$ alcohol and myristic acid can be a member selected from the group consisting of methyl myristate, ethyl myristate, n-propyl myristate, isopropyl myristate, n-butyl myristate, isobutyl myristate and tert-butyl myristate. According to an embodiment, the at least one ester of the $C_2$-$C_5$ alcohol and myristic acid is isopropyl myristate.

According to an embodiment, the ratio of propylene glycol to isopropyl myristate by weight ranges from about 9:1 to about 1:9.

According to an embodiment of the composition, the at least one triester of glycerol and $C_2$-$C_5$ carboxylic acid ranges from about 5% to about 50% by weight, the at least one $C_3$-$C_5$ glycol ranges from about 10% to about 30% by weight, the at least one $C_4$-$C_6$ cyclic carbonate ranges from about 50% to about 75% by weight, the at least one colorant ranges from 0.01% to about 2% by weight, and the at least one ester of the $C_2$-$C_5$ alcohol and myristic acid ranges from about 15% to about 45% by weight, wherein the weight percentages are based on the total weight of the composition.

Another aspect of the present invention is a method of removing nail polish, comprising: (a) providing the nail polish removing composition of the present invention; (b) immersing an absorbent material in the composition, wherein the absorbent material absorbs the composition; (c) contacting the absorbent material to nail polish for a time sufficient to plasticize the nail polish film; and (d) removing the plasticized nail polish film by mechanically rubbing with the absorbent material, wherein the composition comprises one or more phases. The method of removing nail polish may further comprise: (e) shaking the composition to combine phases of the composition, wherein the composition comprises more than one phase.

Still other objects and advantages of the present invention will become readily apparent to those skilled in the art from the following detailed description, where it is shown and describes only the preferred embodiment(s) of the present invention. As will be realized, the invention is capable of other and different embodiments, and its several details are capable of modification in various obvious respects, without departing from the invention. Accordingly, the description is to be regarded as illustrative in nature and not as restrictive.

DETAILED DESCRIPTION OF THE INVENTION

One aspect of the present invention is a nail polish removing composition that is essentially free of acetone and ethyl acetate, and is essentially free of odor. The composition comprises: at least one triester of glycerol and a $C_2$-$C_5$ carboxylic acid, at least one $C_3$-$C_5$ glycol, at least one $C_4$-$C_6$ cyclic carbonate, and optionally at least one colorant.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

The term "nail polish removing", as used herein, means removing a coating of nail polish from the nail and/or area surrounding the nail using a composition. The purpose of "nail polish removing" is either to clean the nails from any nail polish, and/or to prepare the nails for a new layer of nail polish. A further purpose of "nail polish removing" is to remove nail polish from other surfaces that are not on the body (e.g., nail polish that dripped onto a table, floor, clothing, leg, etc.).

The term "at least one", as used herein, means one or more, and thus the term includes individual components as well as mixtures or combinations.

The term "essentially free of acetone and ethyl acetate", as used herein, refers to the contents of the composition of the present invention. "Essentially free of acetone and ethyl acetate" means that, while it is preferred that no acetone or ethyl acetate be present in the composition, it is possible to have very small amounts of acetone and ethyl acetate in the composition of the invention, provided that these amounts do not materially affect the advantageous properties of the composition.

The terms "essentially free of odor" and "odorless", used interchangeably herein, mean that there is no or essentially no detectable level of odor due to common organic solvents that the consumer can perceive. According to the present invention, the odors involved are those of acetone, ethyl acetate, and the various components of the nail polish removing compositions. To determine if a composition is "essentially free of odor" or "odorless", a panel of consumers evaluated whether a scent is noticeable and whether such scent is acceptable.

Nail polish removing is commonly carried out using solvents such as acetone and ethyl acetate, which are very effective solvents. However, the solvents provide a strong odor and tend to remove moisture from the nail and skin near the nail. Therefore, an object of the present invention is to provide a nail polish removing composition that is essentially free of acetone and ethyl acetate and essentially free of odor.

A further object of the present invention is to provide a nail polish removing composition that is essentially free of acetone and ethyl acetate and essentially free of odor, while also providing the benefits of an acetone-based nail polish removing composition.

According to the present invention, the first component of the nail removing composition is at least one triester of glycerol and a $C_2$-$C_5$ carboxylic acid. Glycerol is also commonly referred to as glycerin or glycerine and has the IUPEC name of propane-1,2,3-triol. The $C_2$-$C_5$ carboxylic acid can be selected from acetic acid, propionic acid, butyric acid and valeric acid. Therefore, the at least one triester of glycerol and $C_2$-$C_5$ carboxylic acid can be selected from the group consisting of glycerol triacetate (also referred to as triacetin), glycerol tripropionate, glycerol tributyrate and glycerol trivalerate. Preferably, the at least one triester of glycerol and $C_2$-$C_5$ carboxylic acid is triacetin.

The first component of the nail removing composition is present in various weight percentages, based on the total weight of the composition. For instance, the composition of the present invention comprises the at least one triester of glycerol and $C_2$-$C_5$ carboxylic acid in a range from about 5% to about 50% by weight, based on the total weight of the composition. Preferably, the composition comprises the at least one triester of glycerol and $C_2$-$C_5$ carboxylic acid in a range from about 10% to about 30% by weight, based on the total weight of the composition. More preferably, the composition comprises the at least one triester of glycerol and a $C_2$-$C_5$ carboxylic acid at about 15% by weight, based on the total weight of the composition.

According to the present invention, the second component of the nail polish removing composition is at least one $C_3$-$C_5$ glycol. The at least one $C_3$-$C_5$ glycol may be selected from the group consisting of 1,2-propylene glycol, 1,2-butylene glycol and 1,2-pentylene glycol. Preferably, the at least one $C_3$-$C_5$ glycol is 1,2-propylene glycol, which is commonly known as propylene glycol.

The second component of the nail removing composition is present in various weight percentages, based on the total weight of the composition. For instance, the composition of the present invention comprises the at least one $C_3$-$C_5$ glycol in a range from about 10% to about 30% by weight, based on the total weight of the composition. Preferably, the composition comprises the at least one $C_3$-$C_5$ glycol in a range from about 15% to about 25% by weight, based on the total weight of the composition. More preferably, the composition comprises the at least one $C_3$-$C_5$ glycol at about 20% by weight, based on the total weight of the composition.

According to the present invention, the third component of the nail polish removing composition is at least one $C_4$-$C_6$ cyclic carbonate. The at least one $C_4$-$C_6$ cyclic carbonate can be selected from the group consisting of propylene carbonate, butylene carbonate and pentylene carbonate. Preferably, the at least one $C_4$-$C_6$ cyclic carbonate is propylene carbonate.

The third component of the nail removing composition is present in various weight percentages, based on the total weight of the composition. For instance, the composition of the present invention comprises the at least one $C_4$-$C_6$ cyclic carbonate from about 50% to about 75% by weight, based on the total weight of the composition. Preferably, the composition comprises the at least one $C_4$-$C_6$ cyclic carbonate from about 60% to about 70% by weight, based on the total weight of the composition. More preferably, the composition comprises the at least one $C_4$-$C_6$ cyclic carbonate at about 65% by weight, based on the total weight of the composition.

According to the present invention, the fourth component of the nail polish removing composition is optionally at least one colorant. Suitable colorants would be known to one of ordinary skill in the art. For instance, the suitable colorants according to the instant invention may include dyes, inks, and other soluble colorants. More specifically, a suitable colorant according to the instant invention is FD&C Blue No. 1.

The fourth component of the nail removing composition is optionally present in various weight percentages, based on the total weight of the composition. For instance, the composition of the present invention optionally comprises the at least one colorant in a range from about 0.01% to about 2.0% by weight, based on the total weight of the composition. Preferably, the composition of the present invention optionally comprises the at least one colorant in a range from about 0.02% to about 1.5% by weight, based on the total weight of the composition. More preferably, the composition comprises optionally the at least one colorant at about 0.5% by weight, based on the total weight of the composition.

According to one embodiment, the first, second, third and fourth components of the nail removing composition are present at various weight percentages, such that the at least one triester of glycerol and $C_2$-$C_5$ carboxylic acid ranges from about 5% to about 50% by weight, the at least one $C_3$-$C_5$ glycol ranges from about 10% to about 30% by weight, the at least one $C_4$-$C_6$ cyclic carbonate ranges from about 50% to about 75% by weight, and optionally the at least one colorant ranges from 0.01% to about 2.0% by weight, wherein the weight percentages are based on the total weight of the composition.

Preferably, the first, second, third and fourth components are present in the following weight percentages: the at least one triester of glycerol and $C_2$-$C_5$ carboxylic acid ranges from about 10% to about 30% by weight, the at least one $C_3$-$C_5$ glycol ranges from about 15% to about 25% by weight, the at least one $C_4$-$C_6$ cyclic carbonate ranges from about 60% to about 70% by weight, and optionally the at least one colorant ranges from about 0.02% to about 1.5% by weight, wherein the weight percentages are based on the total weight of the composition.

More preferably, the first, second, third and fourth components are present in the following weight percentages: the at least one triester of glycerol and $C_2$-$C_5$ carboxylic acid at about 15% by weight, the at least one $C_3$-$C_5$ glycol at about 20% by weight, the at least one $C_4$-$C_6$ cyclic carbonate at about 65% by weight, and optionally the at least one colorant at about 0.06% by weight, wherein the weight percentages are based on the total weight of the composition.

According to one embodiment, each of the first, second and third components of the nail removing composition essentially consists a particular compound, such that the at least one triester of glycerol and $C_2$-$C_5$ carboxylic acid consists essentially of triacetin, the at least one $C_3$-$C_5$ glycol consists essentially of propylene glycol, and the at least one $C_4$-$C_6$ cyclic carbonate consists essentially of propylene carbonate.

According to one embodiment, each of the first, second, third and fourth components of the nail polish removing composition is present in various weight percentage ranges, such that triacetin ranges from about 5% to about 50% by weight, propylene glycol ranges from about 10% to about 30% by weight, propylene carbonate ranges from about 50% to about 75% by weight, and optionally the at least colorant ranges from about 0.01% to about 2.0% by weight, wherein the weight percentages are based on the total weight of the composition.

Preferably, each of the first, second, third and fourth components of the nail polish removing composition is present in various weight percentage ranges, such that triacetin ranges from about 10% to about 30% by weight, propylene glycol ranges from about 15% to about 25% by weight, propylene carbonate ranges from about 60% to about 70% by weight, and optionally the at least colorant ranges from about 0.02% to about 1.5% by weight, wherein the weight percentages are based on the total weight of the composition.

More preferably, each of the first, second, third and fourth components of the nail polish removing composition is present at preferred weight percentages, such that triacetin is at about 15% by weight, propylene glycol is at about 20% by weight, propylene carbonate is at about 65% by weight, and optionally the at least one colorant at about 0.5% by weight, wherein the weight percentages are based on the total weight of the composition.

An additional aspect of the present invention is a method of removing nail polish, comprising the following steps (a) providing the nail polish removing composition; (b) immersing an absorbent material in the composition, wherein the absorbent material absorbs the composition; (c) contacting the absorbent material to nail polish for a time sufficient to plasticize the nail polish film; and (d) removing the plasticized nail polish film by mechanically rubbing with the absorbent material, wherein the composition comprises one or more phases. When the composition for removing nail polish has more than one phase, the method may optionally include an additional step: (e) shaking the composition to combine phases of the composition.

The step (a) of the present invention involves providing the nail polish removing composition according to the present invention.

The step (b) of the present invention involves immersing an absorbent material in the composition provided in step (a). The absorbent material may include cotton and/or other absorbent materials that would be readily recognized by one skilled in the art. In one embodiment, the absorbent material is a cotton pad. However, the shape of the absorbent material is not essential. In another embodiment, the absorbent material is a paper-based product. Further, the absorbent material may be completely or partially immersed in the nail polish removing composition. The conditions and length of the immersion will vary depending on the absorbent material used. But, the immersion should allow for the absorbent material to absorb a sufficient amount of the nail polish removing composition to apply the composition to a surface. The absorbent material may be immersed by the end-user or may be immersed during production.

The step (c) of the present invention involves contacting the absorbent material to nail polish for a time sufficient to plasticize the nail polish film. The absorbent material of step (c) must have absorbed a sufficient quantity of the nail polish removing composition. Typically, the absorbent material is contacted with the opening of a container containing the nail polish removing composition, which is inverted twice thereby bringing the composition into contact with the absorbent material. If the nail polish removing composition is in a pump bottle, then typically 2-3 pumps are used to place the composition onto the absorbent material. However, a variety of methods readily appreciated by one skilled in the art would be satisfactory to provide a quantity of the nail polish removing composition onto the absorbent material. Further, typically, the absorbent material would be in contact with the nail polish film for a minimum of 5 seconds. Preferably, the absorbent material would be in contact with the nail polish film for a between 5-10 seconds to plasticize the nail polish film.

The step (d) of the present invention involves removing the plasticized nail polish film by mechanically rubbing with the absorbent material. The mechanical force required to remove the plasticized nail polish film will vary depending at least on the type of nail polish applied, the thickness of the nail polish film, the duration in which mechanical force is applied, and characteristics of the nail itself.

The nail polish removing composition may exist in more than one phase. If the nail polish removing composition contains two or more phases, the method may include step (e) shaking the composition to combine phases of the composition.

While the nail polish removing composition can be used for removing nail polish, the present invention is not necessarily limited to nail polish removing. Rather, the nail polish removing composition can be used for a variety of additional purposes include, but not limited to, the removal of transfer resistant cosmetics. Non-limiting examples of transfer resistant cosmetics include long-wearing mascara and long-wearing lipstick. Further, the nail polish removing composition can simply be used as a nail moisturizer and thus does not necessarily have to be used only to remove nail polish. Moreover, the nail polish removing composition can be used to remove nail polish from a variety of surfaces including, but not limited to: surfaces on the body, such as nails, cuticles, fingers, toes, etc.; and other surfaces, such as wood, glass, tile, cloth, etc.

The invention is illustrated in greater details in the following examples, which are exemplary and therefore not limiting.

Example 1

Exemplary Formulation

The exemplary formulation of the composition is presented herein as an illustration of the various components that are included in the nail polish removing composition that is acetone and ethyl acetate free and is free of odor. All the numbers in the table below are weight percentages, based on the total weight of the composition. The exemplary formulation in the table below is a single phase formulation.

| INCI Name of Component | Formulation 1 |
| --- | --- |
| Triacetin | 14.94 |
| Propylene Glycol | 20 |
| Propylene Carbonate | 65 |
| Isopropyl Myristate | 0 |
| Colorant | 0.06 |

Example 2

Exemplary Formulation

The exemplary formulation of the composition is presented herein as an illustration of the various components that are included in the nail polish removing composition that is acetone and ethyl acetate free and is free of odor. All the numbers in the table below are weight percentages, based on the total weight of the composition. The exemplary formulation in the table below is a bi-phase formulation.

| INCI Name of Component | Formulation 2 |
| --- | --- |
| Triacetin | 10 |
| Propylene Glycol | 25 |
| Propylene Carbonate | 40 |
| Isopropyl Myristate | 25 |
| Colorant | 0 |

Example 3

Consumer Flash Test

A consumer flash test was conducted that compared two formulations. One of the formulations was a formulation according to the present invention that is referred to in this example as the Odor Free Remover, the formulation of which is set forth in the table below. All the numbers in the table below are the approximate weight percentages, based on the total weight of the composition.

| INCI Name of Component | Odor Free Remover |
| --- | --- |
| Triacetin | 15 |
| Propylene Glycol Ideal | 20 |
| Propylene Carbonate | 65 |
| Colorant | 0.5 |

The other formulation was an acetone-based comparative formulation that is referred to in this example as the Acetone Remover, the formulation of which is set forth in the table below. All the numbers in the table below are the approximate weight percentages, based on the total weight of the composition.

| INCI Name of Component | Acetone Remover |
| --- | --- |
| Acetone | 85 |
| Water | 14.94 |
| Colorant | 0.06 |

Twenty women between the ages of 18 and 65, who self-apply nail polish at home at least twice a month, participated in the test. The participants self-applied Essie® Really Red nail polish at home, and wore the nail polish for a period of at least 24 hours. The participants then removed the nail polish using either the Odor Free Remover or Acetone Remover. The application and removal process was then repeated for a second time, again using the same remover as the first time. The participants then repeated this entire process using either the Odor Free Remover or Acetone Remover, whichever was not used previously; and subsequently returned to the testing center for a follow-up interview to compare the Odor Free Remover and Acetone Remover according to various criteria and attributes.

The participants were asked to provide the overall preference between the Odor Free Remover and the Acetone Remover. The overall preference was equally split between the Odor Free Remover and the Acetone Remover. Further, the participants found that the Acetone Remover removed the polish more easily and efficiently. However, the participants found the Odor Free Remover to be gentler during removal by a significant margin. A summary of the results of the interviews is provided in the table below.

|  | Frequency | Percent |
|---|---|---|
| Overall preference |  |  |
| Odor-Free Remover | 10 | 50% |
| Acetone Remover | 10 | 50% |
| Base |  | 20 |
| Removed polish more easily |  |  |
| Odor-Free Remover | 6 | 30% |
| Acetone Remover | 13 | 65% |
| No response | 1 | 5% |
| Base |  | 20 |
| Removed polish more efficiently |  |  |
| Odor-Free Remover | 7 | 35% |
| Acetone Remover | 12 | 60% |
| No response | 1 | 5% |
| Base |  | 20 |
| More gentle during removal |  |  |
| Odor-Free Remover | 17 | 85% |
| Acetone Remover | 2 | 10% |
| No response | 1 | 5% |
| Base |  | 20 |

Concerning the gentleness of the product, 75% of the participants felt that the Odor Free Remover was very gentle whereas only 15% of the participants found the Acetone Remover to be very gentle. A summary of the results of the interviews is provided in the table below.

|  | Odor-Free | | Acetone | |
|---|---|---|---|---|
| Gentleness of product | Frequency | Percent | Frequency | Percent |
| Very gentle | 15 | 75% | 3 | 15% |
| Somewhat gentle | 2 | 10% | 6 | 30% |
| Neither gentle nor harsh | 1 | 5% | 8 | 40% |
| Somewhat harsh | 1 | 5% | 2 | 10% |
| Very harsh | 1 | 5% | 1 | 5% |
| Base | 20 | | 20 | |

The participants also felt that the Odor Free Remover provided less scent than the Acetone Remover. Further, the participants found the scent intensity and scent acceptability of the Odor Free Remover to be significantly favorable as compared to the Acetone Remover. A summary of the results of the interviews is provided in the table below.

|  | Odor-Free | | Acetone | |
|---|---|---|---|---|
|  | Frequency | Percent | Frequency | Percent |
| Scent? |  |  |  |  |
| Yes | 6 | 30% | 15 | 75% |
| No | 14 | 70% | 5 | 25% |
| Base | 20 | | 20 | |
| Scent intensity |  |  |  |  |
| Much too intense | — | — | 3 | 20% |
| Somewhat too intense | — | — | 6 | 40% |
| Just the right intensity | 6 | 100% | 5 | 33% |
| Somewhat too subtle | — | — | — | — |
| Much too subtle | — | — | 1 | 7% |
| Base | 6 | | 15 | |
| Scent acceptability |  |  |  |  |
| Very acceptable | 5 | 83% | 2 | 13% |
| Somewhat acceptable | 1 | 17% | 3 | 20% |
| Neither acceptable nor unacceptable | — | — | 3 | 20% |
| Somewhat unacceptable | — | — | 3 | 20% |
| Very unacceptable | — | — | 4 | 27% |
| Base | 6 | | 15 | |

Finally, the participants were asked about the condition of their nails after removal of the nail polish. The participants felt that the Odor Free Remover provided much better moisturizing properties and less nail staining properties than the Acetone Remover. The Acetone Remover, however, provided less residue on the nail. A summary of the results of the interviews is provided in the table below.

|  | Odor-Free | | Acetone | |
|---|---|---|---|---|
|  | Frequency | Percent | Frequency | Percent |
| Nail/cuticle after removal |  |  |  |  |
| Much drier | 1 | 5% | 7 | 35% |
| Somewhat drier | — | — | 6 | 30% |
| Neither drier nor more moisturized | 2 | 10% | 4 | 20% |
| Somewhat more moisturized | 7 | 35% | 2 | 10% |
| Much more moisturized | 10 | 50% | 1 | 5% |
| Base | 20 | | 20 | |
| Residue on nails |  |  |  |  |
| Yes | 12 | 60% | 6 | 30% |
| No | 8 | 40% | 14 | 70% |
| Base | 20 | | 20 | |
| Residue acceptability |  |  |  |  |
| Very acceptable | 3 | 25% | — | — |
| Somewhat acceptable | 1 | 8% | — | — |
| Neither acceptable nor unacceptable | 1 | 8% | 1 | 17% |
| Somewhat unacceptable | 5 | 42% | 3 | 50% |
| Very unacceptable | 2 | 17% | 2 | 33% |
| Base | 12 | | 6 | |
| Nail staining |  |  |  |  |
| No staining at all (1) | 3 | 15% | 3 | 15% |
| 2 | 7 | 35% | 6 | 30% |
| 3 | 2 | 10% | 4 | 20% |
| 4 | 1 | 5% | 1 | 5% |
| 5 | 3 | 15% | 1 | 5% |
| 6 | 3 | 15% | 1 | 5% |
| 7 | — | — | 1 | 5% |
| 8 | 1 | 5% | 2 | 10% |
| A lot of staining (9) | — | — | 1 | 5% |
| Mean | 3.4 | | 3.7 | |
| Base | 20 | | 20 | |

Example 4

Evaluation of Wear of New Polish Application by Cosmetologist

To evaluate the effect of nail polish removers on the wear of nail polish, with and without washing hands after the removal of the previous nail polish and before a new application, further study was undertaken. Twelve models wore Essie® Eu-Really Red nail polish for 24 hours, which is the same nail polish used in Example 3. A Cosmetologist then removed the nail polish from one hand with the Odor Free Remover described in Example 3 and from the other hand with the Acetone Remover described in Example 3.

In one test method, after removal of the nail polish, six of the models washed their hands with soap and water. Then, the Cosmetologist wiped the nail of each of the six models with an alcohol wipe and reapplied the nail polish. In another test method, nail polish was applied directly to the remaining six other models' nails immediately after removal of the nail polish without washing the models' hands or using alcohol wipes. The Cosmetologist subsequently evaluated the 5-day wear of the nail polish finding that both the Odor Free Remover and Acetone Remover had the same effect on the 5-day wear of the nail polish under both applications. Further, the Cosmetologist found that the Odor Free Remover was more oily and more difficult to remove, and also left the nails and the cuticles shiner and stickier in comparison with the Acetone Remover. However, the Acetone Remover left a white residue and dry appearance on the cuticle.

The present invention of the nail polish removing composition has achieved several desirable advantages from the perspective of the consumers. First, the composition according to the invention is essentially acetone and ethyl acetate free. Using a combination involving a triester of glycerol and a $C_2$-$C_5$ carboxylate acid such as triacetate, a $C_3$-$C_5$ glycol such as propylene glycol, and a $C_4$-$C_6$ cyclic carbonate such as propylene carbonate has realized a nail polish removing system that is free of acetone and ethyl acetate. According to the consumer test, the composition of the invention achieved an overall satisfactory rating. The composition was recognized by the consumers as having gentle removal capacity.

Second, the composition according to the invention is essentially odor free. As noted above, the combination of components such as triacetate, propylene glycol and propylene carbonate as a nail polish removing system is essentially odorless. About only one third of the consumers noticed any scent of the composition according to the invention. Consumers preferred the composition of the invention for less scent in the formulation, and all consumers found the scent of the composition according to the invention acceptable.

Third, in comparison of acetone-based nail polish removers, the composition according to the invention is equally preferred as nail polish remover.

Fourth, a shiny film is left on the nail after using the nail polish removing composition. This shiny film provides a moisturizing effect to the nail and thus prevents the formation of a white coat that usually comes with dry nail. According to 5-day wear comparative studies under Example 4, it was found that the shiny film resulted from using the composition of the invention does not affect the nail polish that is subsequently applied.

The foregoing description illustrates and describes the invention. Additionally, the foregoing description shows and describes only the preferred embodiment(s) but, as mentioned above, it is to be understood that it is capable to use in various other combinations, modifications, and environments and is capable of changes or modifications within the scope of the invention concepts as expressed herein, commensurate with the above teachings and/or skill or knowledge of the relevant art. The embodiments described herein above are further intended to explain best modes known by the applicants and to enable others skilled in the art to utilize the disclosure in such, or other, embodiments and with the various modifications required by the particular applications or uses thereof. Accordingly, the description is not intended to limit the invention to the form disclosed herein. Also, it is intended that the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent applications incorporated herein by reference, the present disclosure controls.

What is claimed is:

1. A nail polish remover, wherein said nail polish remover contains a composition, said composition comprising:
   at least one triester of glycerol and $C_2$-$C_5$ carboxylic acid,
   at least one $C_3$-$C_5$ glycol,
   at least one $C_4$-$C_6$ cyclic carbonate, and
   optionally at least one colorant,
   wherein the composition is essentially free of acetone and ethyl acetate,
   further wherein the composition comprises the at least one $C_3$-$C_5$ glycol in a range from about 10% to about 30% by weight, based on the total weight of the composition, and
   further wherein the composition is essentially free of odor.

2. The nail polish remover according to claim 1, wherein the at least one triester of glycerol and $C_2$-$C_5$ carboxylic acid is selected from the group consisting of triacetin, glycerol tripropionate, glycerol tributyrate and glycerol trivalerate.

3. The nail polish remover according to claim 1, wherein the at least one triester of glycerol and $C_2$-$C_5$ carboxylic acid comprises triacetin.

4. The nail polish remover according to claim 1, where the composition comprises the at least one triester of glycerol and $C_2$-$C_5$ carboxylic acid in a range from about 5% to about 50% by weight, based on the total weight of the composition.

5. The nail polish remover according to claim 1, wherein the at least one $C_3$-$C_5$ glycol is selected from the group consisting of 1,2-propylene glycol, 1,2-butylene glycol and 1,2-pentylene glycol.

6. The nail polish remover according to claim 1, wherein the at least one $C_3$-$C_5$ glycol comprises 1,2-propylene glycol.

7. The nail polish remover according to claim 1, wherein the at least one $C_4$-$C_6$ cyclic carbonate is selected from the group consisting of propylene carbonate, butylene carbonate and pentylene carbonate.

8. The nail polish remover according to claim 1, wherein the at least one $C_4$-$C_6$ cyclic carbonate comprises propylene carbonate.

9. The nail polish remover according to claim 1, wherein the composition comprises the at least one $C_4$-$C_6$ cyclic carbonate in a range from about 50% to about 75% by weight, based on the total weight of the composition.

10. A nail polish remover, wherein said nail polish remover contains a composition, said composition comprising:
    from about 5% to about 50% by weight, based on the total weight of the composition, of at least one triester of glycerol and $C_2$-$C_5$ carboxylic acid,
    from about 10% to about 30% by weight, based on the total weight of the composition, of at least one $C_3$-$C_5$ glycol,
    from about 50% to about 75% by weight, based on the total weight of the composition, of at least one $C_4$-$C_6$ cyclic carbonate, and
    optionally from 0.01% to about 2% by weight, based on the total weight of the composition, of at least one colorant,
    wherein the composition is essentially free of acetone and ethyl acetate, and
    further wherein the composition is essentially free of odor.

11. The nail polish remover according to claim 1, wherein the at least one triester of glycerol and $C_2$-$C_5$ carboxylic acid comprises triacetin, the at least one $C_3$-$C_5$ glycol comprises propylene glycol, and the at least one $C_4$-$C_6$ cyclic carbonate comprises propylene carbonate.

12. The nail polish remover according to claim 11, wherein the triacetin ranges from 5% to about 50% by weight, the propylene glycol ranges from about 10% to about 30% by weight, and the propylene carbonate ranges from about 50% to about 75% by weight, further wherein the weight percentages are based on the total weight of the composition.

13. The nail polish remover according to claim 1, further comprising at least one ester of a $C_2$-$C_5$ alcohol and myristic acid.

14. The nail polish remover according to claim 13, wherein the at least one ester of a $C_2$-$C_5$ alcohol and myristic acid is selected from the group consisting of methyl myristate, ethyl myristate, n-propyl myristate, isopropyl myristate, n-butyl myristate, isobutyl myristate and tert-butyl myristate.

15. The nail polish remover according to claim 13, wherein the at least one $C_3$-$C_5$ glycol comprises propylene glycol, and the at least one ester of a $C_2$-$C_5$ alcohol and myristic acid comprises isopropyl myristate.

16. The nail polish remover according to claim 15, wherein the ratio of propylene glycol to isopropyl myristate by weight ranges from about 9:1 to about 1:9.

17. A nail polish remover, wherein said nail polish remover contains a composition, said composition comprising:
   from about 5% to about 50% by weight, based on the total weight of the composition, of at least one triester of glycerol and $C_2$-$C_5$ carboxylic acid,
   from about 10% to about 30% by weight, based on the total weight of the composition, of at least one $C_3$-$C_5$ glycol,
   from about 50% to about 75% by weight, based on the total weight of the composition, of at least one $C_4$-$C_6$ cyclic carbonate,
   from about 15% to about 45% by weight, based on the total weight of the composition, at least one ester of a $C_2$-$C_5$ alcohol and myristic acid; and
   optionally from 0.01% to about 2% by weight, based on the total weight of the composition, of at least one colorant,
   wherein the composition is essentially free of acetone and ethyl acetate, and
   further wherein the composition is essentially free of odor.

18. A method of removing nail polish, comprising:
   (a) providing a nail polish remover, wherein said nail polish remover contains a composition, said composition comprising:
   at least one triester of glycerol and $C_2$-$C_5$ carboxylic acid,
   at least one $C_3$-$C_5$ glycol,
   at least one $C_4$-$C_6$ cyclic carbonate, and
   optionally at least one colorant,
   wherein the composition is essentially free of acetone and ethyl acetate, and
   wherein the composition is essentially free of odor;
   (b) immersing an absorbent material in the nail polish remover, wherein the absorbent material absorbs the nail polish remover;
   (c) contacting the absorbent material containing the nail polish remover to nail polish for a time sufficient to plasticize the nail polish film; and
   (d) removing the plasticized nail polish film by mechanically rubbing with the absorbent material,
   wherein the composition contained in the nail polish remover comprises one or more phases.

19. The method of removing nail polish according to claim 18, wherein the composition contained in the nail polish remover comprises two or more phases, and further wherein the method comprises the additional step of
   (e) shaking the nail polish remover to combine said two or more phases of the composition.

* * * * *